United States Patent
Kada et al.

(10) Patent No.: US 7,018,462 B2
(45) Date of Patent: Mar. 28, 2006

(54) ORGANIC ACID METAL SALT AND COATING LIQUID CONTAINING THE SAME FOR FORMING A METAL OXIDE FILM

(75) Inventors: Koji Kada, Osaka (JP); Hideyuki Nomura, Kyoto (JP); Kayoko Honda, Hyogo (JP); Kouhei Sawada, Hyogo (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 10/695,037

(22) Filed: Oct. 28, 2003

(65) Prior Publication Data

US 2004/0144286 A1    Jul. 29, 2004

(30) Foreign Application Priority Data

Oct. 28, 2002   (JP) ............................. 2002-312662

(51) Int. Cl.
   *C09D 191/00*   (2006.01)
   *C08L 91/00*    (2006.01)
   *C07C 51/41*    (2006.01)

(52) U.S. Cl. ...................... 106/243; 554/156; 554/157; 562/606

(58) Field of Classification Search ................ 106/243; 554/156, 157; 562/606

See application file for complete search history.

(56) References Cited

U.S. PATENT DOCUMENTS

| | | | | |
|---|---|---|---|---|
| 3,899,588 A | * | 8/1975 | Skov et al. | .................. 514/557 |
| 4,235,794 A | * | 11/1980 | Rieber et al. | .................. 554/73 |
| 5,180,850 A | * | 1/1993 | Cavazza | ..................... 562/606 |

FOREIGN PATENT DOCUMENTS

| | | |
|---|---|---|
| JP | 6-162920 | 6/1994 |
| JP | 8-329844 | 12/1996 |
| JP | 9-12940 | 1/1997 |
| JP | 9-95627 | 4/1997 |
| JP | 9-129141 | 5/1997 |
| JP | 9-208851 | 8/1997 |

* cited by examiner

*Primary Examiner*—David Brunsman
(74) *Attorney, Agent, or Firm*—Amin & Turocy, LLP

(57) ABSTRACT

The present invention provides an organic acid metal salt obtained by reacting a saturated monocarboxylic acid or its salt and an inorganic magnesium compound. The saturated monocarboxylic acid or its salt contains at least 97 wt % of a saturated monocarboxylic acid having 4 to 10 carbon atoms or its salt, and the organic acid metal salt contains at least 99 wt % of an organic acid magnesium salt. This organic acid metal salt consists essentially of an organic acid magnesium salt, and has excellent solubility in an alcohol solvent or a mixed solvent containing at least 5 wt % of an alcohol solvent and excellent temporal stability when being formed into a coating liquid for forming a magnesium oxide film. A coating film obtained from this coating liquid has excellent uniformity and provides a highly transparent magnesium oxide film having a thickness suitable for practical use by baking. At the time of baking after coating, there is no solvent residue in the film and environmental pollutant gas such as NOx is not emitted.

20 Claims, No Drawings

ORGANIC ACID METAL SALT AND COATING LIQUID CONTAINING THE SAME FOR FORMING A METAL OXIDE FILM

BACKGROUND OF THE INVENTION

1. Field of the Invention

The present invention relates to an organic acid magnesium salt suitable for forming a magnesium oxide film used as a protective film for a dielectric material in a plasma display panel (PDP) and the like by the coating pyrolysis method.

2. Description of the Related Art

Magnesium oxide films are utilized in a wide range of applications such as protective films for PDPs, insulating films, catalyst films, and surface protective films. Conventionally, films of metal oxide including magnesium oxide are formed by physical film forming methods such as sputtering and vacuum evaporation. With these methods, a uniform, dense and highly crystalline film can be obtained. On the other hand, since the films are formed in a vacuum, a large and complex, and expensive apparatus is necessary. Furthermore, since production is performed in a batch manner, the production efficiency is poor, and the production cost is high.

In contrast to physical film forming methods, the coating pyrolysis method is employed by which a metal oxide film can be formed in a simple process without an expensive and complex apparatus.

In the film formation by the coating pyrolysis method, various compounds of alkaline-earth metals are used. For example, compositions containing the following compounds for forming a metal oxide (magnesium oxide) film are known: MgO particles and a MgO precursor that forms MgO by baking (Japanese Laid-Open Patent Publication Nos. 9-12940 and 9-208851), and an alkoxide of an alkaline-earth metal (e.g., magnesium) (Japanese Laid-Open Patent Publication Nos. 6-162920 and 8-329844).

However, the compositions (coating liquids) for forming a metal oxide film generally have poor temporal stability so that a uniform film cannot be obtained, or only a film having a small thickness can be obtained.

Furthermore, in addition to the above-described magnesium compounds, organic acid magnesium salts are known as compounds that can be contained in a composition used in the coating pyrolysis method. However, in general, organic acid magnesium salts have poor solubility in solvents. For example, when they are formed into a coating liquid using an alcohol solvent, opaqueness may occur or a precipitate may be generated. For this reason, a transparent coating liquid without opaqueness or a precipitate has been studied by using various additives.

For example, in Japanese Laid-Open Patent Publication No. 9-95627, a coating liquid is prepared that contains an organic acid magnesium salt, a polyhydric alcohol acetic acid derivative as a solvent, and an additive such as a thickener. Furthermore, in Japanese Laid-Open Patent Publication No. 9-129141, a coating liquid containing an organic acid magnesium salt, a poyhydric alcohol derivative, an organic acid, an amine, and an additive such as a thickener is prepared. However, there is the drawback that the temporal stability of these coating liquids is insufficient.

As mentioned above, the coating liquid containing an organic acid magnesium salt has the drawback that the coating liquid becomes opaque, when a widely used solvent such as an alcohol solvent or the like is employed, and thus, the coating film becomes opaque or the coating film cannot be formed. Even though a transparent coating liquid is formed by employing the above-mentioned technique, the temporal stability of the coating liquid is insufficient.

SUMMARY OF THE INVENTION

The organic acid metal salt of the present invention is obtained by reacting a saturated monocarboxylic acid or its salt and an inorganic magnesium compound, wherein the saturated monocarboxylic acid or its salt contains at least 97 wt % of a saturated monocarboxylic acid having 4 to 10 carbon atoms or its salt, and the organic acid metal salt contains at least 99 wt % of an organic acid magnesium salt.

In a preferred embodiment, the saturated monocarboxylic acid having 4 to 10 carbon atoms is a saturated linear monocarboxylic acid.

In a preferred embodiment, the organic acid metal salt has characteristics in that a solution prepared by dissolving the organic acid metal salt in ethanol at a concentration of 40 wt % is clear after the solution is allowed to stand at 30° C. for one hour.

The method for producing an organic acid metal salt of the present invention comprises the step of, reacting an inorganic magnesium compound with a saturated monocarboxylic acid or its salt in a molar ratio of 1:2 to 1:3, wherein the saturated monocarboxylic acid or its salt contains at least 97 wt % of a saturated monocarboxylic acid or its salt having 4 to 10 carbon atoms, and wherein the organic acid metal salt contains at least 99 wt % of an organic acid magnesium salt.

In a preferred embodiment, the saturated monocarboxylic acid having 4 to 10 carbon atoms is a saturated linear monocarboxylic acid.

In a preferred embodiment, the saturated monocarboxylic acid or its salt is a saturated monocarboxylic acid.

In a preferred embodiment, the reaction is performed in a solvent that is water or an organic solvent containing at least 10 wt % of water.

In a preferred embodiment, the method further comprises the step of removing the solvent at 80° C. or less.

In a preferred embodiment, the inorganic magnesium compound is magnesium hydroxide.

The coating liquid for forming a magnesium oxide film of the present invention comprises 100 parts by weight of an organic solvent selected from the group consisting of an alcohol solvent and a mixed solvent that contains an alcohol solvent, and 1 to 100 parts by weight of the above-mentioned organic acid metal salt.

In a preferred embodiment, the mixed solvent is a mixed solvent of an alcohol solvent and a solvent selected from the group consisting of an aliphatic hydrocarbon solvent, an ester solvent, an ether solvent and a halogen solvent.

In a preferred embodiment, the organic solvent is a mixed solvent that contains at least 5 wt % of an alcohol solvent.

In a preferred embodiment, the alcohol solvent is monohydric or polyhydric alcohol having 1 to 8 carbon atoms.

In a preferred embodiment, each of the boiling point of the alcohol solvent and the boiling point of the organic solvent contained in the mixed solvent is 70° C. or more and 200° C. or less.

Thus, the invention described herein makes possible the advantages of: providing an organic acid metal salt consisting essentially of an organic acid magnesium salt that can form a magnesium oxide film having higher strength, excellent transparency, and a sufficient thickness for practical use by the coating pyrolysis method; providing a method for producing the organic acid metal salt mentioned above; and a coating liquid that contains the organic acid metal salt, and that can form the magnesium oxide film having the above-mentioned excellent characteristics, wherein the coating liquid is excellent in temporal stability.

DESCRIPTION OF THE PREFERRED EMBODIMENT

The organic acid metal salt of the present invention is synthesized by a saturated monocarboxylic acid or its salt (component a) and an inorganic magnesium compound (component b), and consists essentially of an organic acid magnesium salt. The organic acid metal salt contains at least 99 wt % of an organic acid magnesium salt.

It is necessary that the component a contains at least 97 wt % of a saturated monocarboxylic acid having 4 to 10 carbon atoms or its salt. Preferably, the content of the saturated monocarboxylic acid is at least 98 wt %, and more preferably at least 99 wt %.

Organic acid magnesium salts obtained by using a saturated carboxylic acid having 3 carbon atoms or less tend to be crystallized and form white fine particles when they are formed into a coating liquid for forming magnesium oxide films. Therefore, it is difficult to apply the coating liquid uniformly. Alternatively, the organic acid magnesium salt is in a dissolved state during application, but after forming a coating film, the coating film tends to become opaque in the process of drying and a magnesium oxide film obtained by baking the same also tends to become opaque. Organic acid magnesium salts obtained by using a carboxylic acid having 11 carbon atoms or more have poor solubility in a solvent so that they are difficult to form into a coating liquid.

The saturated monocarboxylic acid having 4 to 10 carbon atoms or its salt is obtained from a natural source or produced by chemical synthesis. However, such a saturated monocarboxylic acid or its salt contains impurities that have not been removed by distillation in a purification stage. For example, paraffin compounds such as decane, dodecane and tridecane, ketone compounds such as 2-undecanone, long chain alcohols, and long chain aldehydes may be contained. Furthermore, carboxylic acids having 3 carbon atoms or less, or those having at least 11 carbon atoms derived from the raw material used for synthesis may be contained.

These impurities are attached to unreacted inorganic magnesium compounds and an organic acid magnesium salt produced by a reaction during the synthesis of the organic acid magnesium salt, and form adhesive impurities. The adhesive impurities are hardly dissolved in an organic solvent, and hardly removed even by purification, and remains in the resultant product. When such impurities in total exceed 3 wt %, a precipitate or opaqueness occurs when preparing a coating liquid, so that an organic acid magnesium salt having a predetermined concentration cannot be prepared. In addition, this may cause a magnesium oxide film to be opaque.

In the present invention, saturated monocarboxylic acids having 4 to 10 carbon atoms are preferably employed. Examples of the saturated monocarboxylic acids having 4 to 10 carbon atoms include butyric acid, isobutyric acid, valeric acid, isovaleric acid, caproic acid, 2-ethyl butyric acid, enanthic acid, caprylic acid, pelargonic acid, and capric acid. Saturated linear monocarboxylic acids having 4 to 10 carbon atoms are preferable. An organic acid magnesium salt synthesized by using a saturated branched monocarboxylic acid is hardly decomposed due to its molecular structure. The starting temperature and the ending temperature of the thermal decomposition of such a magnesium salt are higher than those of the organic acid magnesium salt synthesized by using a saturated linear monocarboxylic acid, respectively. Therefore, higher temperatures are necessary for baking a coating film derived from a coating liquid containing the salt, which is not economical. The saturated monocarboxylic acid used in the present invention may be employed alone or employed in combination of two or more.

The saturated monocarboxylic acid salt used as the component a is a compound obtained by reacting a saturated monocarboxylic acid as described above and an alkali in an aqueous solvent. Examples of the saturated monocarboxylic acid salt include alkali metal salts such as sodium salts and potassium salts; ammonium salts; amine salts such as diethyl amine salts, triethyl amine salts and ethanol amine salts. Most preferable examples are ammonium salts and amine salts. When an alkali metal salt is employed, a saturated fatty acid alkali metal salt may remain in the resultant organic acid metal salt that consists essentially of an organic acid magnesium salt, which may affect adversely the electrical characteristics and the film strength of the magnesium oxide film obtained by baking.

The purity of the saturated monocarboxylic acid or its salt used in the present invention can be measured by gas chromatography, a gas chromatography/mass spectrometry, or the like.

When a saturated monocarboxylic acid is used as the component a, magnesium hydroxide, magnesium oxide, magnesium carbonate or the like is used as the inorganic magnesium compound, which is the component b. In view of easy handling of the solution during reaction and uniform proceeding of the reaction, magnesium hydroxide is preferably used. On the other hand, when a saturated monocarboxylic acid salt is used as the component a, a water-soluble inorganic magnesium compound such as magnesium chloride or magnesium sulfate can be used as the component b. In view of the removability of a by-product salt, magnesium sulfate that forms sodium sulfate, which is easily soluble in water, is preferably employed.

In general, the inorganic magnesium compound used as a raw material contains a metal compound such as a calcium compound as an impurity. When an organic acid metal salt is synthesized by using a raw material containing such a metal compound as impurity, this metal compound is also reacted with the saturated monocarboxylic acid so as to produce an organic acid metal salt. It is difficult to separate and remove the thus produced organic acid metal salt from the resultant organic acid magnesium salt. Therefore, it is preferable that the ratio of the magnesium with respect to the total metal contained in the inorganic magnesium compound (component b) is 99 wt % or more. When an inorganic magnesium compound having a content of magnesium of less than 99 wt % with respect to the total metal content is used as a starting raw material, the obtained organic acid metal salt becomes opaque when being dissolved in a solvent such as an alcohol. A coating liquid containing such an organic acid metal salt has poor temporal stability, and a precipitate is formed. Furthermore, when a magnesium oxide film is formed by using this coating liquid containing the organic acid metal salt, the resultant magnesium oxide film has opaqueness and cracks.

The contents of the magnesium and other metals in the organic acid metal salt of the present invention can be measured by atomic absorption spectrometry, fluorescent X-ray analysis, inductive coupling plasma emission analysis or the like.

The organic acid metal salt of the present invention can be obtained by reacting the component a containing 97 wt % or more of the saturated monocarboxylic acid having 4 to 10 carbon atoms and the inorganic magnesium compound (component b), preferably in a manner described later.

The organic acid metal salt of the present invention contains 99 wt % or more, more preferably 99.5 wt % or more of an organic acid magnesium salt. As described above, in the reaction of the saturated monocarboxylic acid (component a) and the inorganic magnesium compound (component b), which are the starting materials, impurities derived from materials contained in these starting materials cannot be completely removed, and therefore organic acid metal salts derived from metals other than magnesium (e.g., calcium) remain in the finally obtained product. When the content of the organic acid magnesium salt in the organic acid metal salt is less than 99 wt %, the solubility of the organic acid metal salt in a solvent is poor and opaqueness occurs. Furthermore, when a magnesium oxide film is formed by using a coating liquid for forming a film containing this organic acid metal salt, the resultant film has opaqueness and cracks.

It is preferable that the organic acid metal salt of the present invention contains magnesium in a ratio of 99 wt % or more, and more preferably 99.5 wt % or more, with respect to the total metal. When impurity metals other than magnesium are contained in a ratio of more than 1 wt %, opaqueness occurs at the time of dissolution of the organic acid metal salt. Furthermore, a coating liquid containing such an organic acid metal salt having a large amount of impurity metals has poor temporal stability and tends to form a precipitate. In addition, the magnesium oxide film obtained from the coating liquid may be opaque and cracks may occur.

A method for producing the organic acid metal salt of the present invention includes the step of reacting a saturated carboxylic acid containing 97 wt % or more of a saturated monocarboxylic acid having 4 to 10 carbon atoms or its salt (component a) and an inorganic magnesium compound (component b) in a solvent. In this method, in general, after the reaction, the solvent used is removed so that the organic acid metal salt is isolated.

In the salt formation reaction, the reaction is carried out by using 2 to 3 moles, preferably 2 to 2.5 moles of the saturated monocarboxylic acid or its salt having 4 to 10 carbon atoms with respect to 1 mole of the inorganic magnesium compound. It is most preferable to use the saturated monocarboxylic acid or its salt in an amount that is slightly larger (e.g., 1 to a few % larger, more specifically about 2.02 to 2.1 moles) than the mole equivalent (i.e., two moles of a saturated monocarboxylic acid or its salt with respect to one mole of magnesium compound), because the amount of the saturated monocarboxylic acid that remains can be reduced as much as possible. When the saturated monocarboxylic acid or its salt in an amount of less than 2 moles reacts with one mole of the inorganic magnesium compound, the reaction does not completely proceed, which may cause opaqueness when the coating liquid is prepared. Furthermore, when a magnesium oxide film is formed by using the resultant coating liquid and baked, opaqueness and cracks occur. When the saturated monocarboxylic acid or its salt in an amount of more than 3 moles is reacted with one mole of the inorganic magnesium compound, an excess amount of the saturated carboxylic acid or its salt remains, which disadvantageously affects the production efficiency and cost.

There are a direct method and a double decomposition method as methods for producing the organic acid metal salt of the present invention. The direct method includes a process of reacting directly a magnesium compound such as magnesium oxide, magnesium hydroxide and a carboxylic acid. The double decomposition method includes a process of mixing an aqueous solution of a magnesium salt such as magnesium chloride and a solution of a carboxylic acid salt such as a sodium carboxylate salt, and effecting salt exchange. In the present invention, either method can be used, but the direct method is preferable. This is because in the double decomposition method, inorganic metal salts (e.g., sodium chloride) other than magnesium salt form as by-product impurities, whereas in the direct method, such impurities are not produced.

When the direct method is employed, it is preferable to use magnesium hydroxide as the magnesium compound. For example, when magnesium oxide is used as a raw material, the reaction may not completely proceed. In such a case, the solubility of the organic acid metal salt in a solvent is reduced significantly.

In the salt formation reaction, water or an organic solvent containing 10 wt % or more of water is preferably used as a solvent. Water serves as a catalyst for promoting a reaction and also serves as a solvent for allowing a reaction to proceed uniformly. When water is only contained in a ratio of less than 10 wt % in the organic solvent used for a reaction, the function as a catalyst cannot be exerted sufficiently, and the reaction proceeds in a very low speed, and the organic acid metal salt as the final product has a poor solubility in an organic solvent.

In the salt formation reaction, as the organic solvent that can be used by being mixed with water, a hydrocarbon solvent, an alcohol solvent, an ester solvent, or an ether solvent is preferable. Examples of the hydrocarbon solvent include n-hexane, n-octane, cyclohexane, toluene, and xylene. Examples of the alcohol solvent include methanol, ethanol, propanol, butanol, ethylene glycol, and propylene glycol. Examples of the ester solvent include ethyl acetate, butyl acetate, ethylene glycol monomethyl ether acetate, and propylene glycol monomethyl ether acetate. Examples of the ether solvent include ethylene glycol monomethyl ether, ethylene glycol monoethyl ether, and propylene glycol monomethyl ether. These solvents can be used alone or in combination of two or more.

The reaction temperature in the salt formation reaction is preferably 40° C. to 80° C., more preferably 40° C. to 70° C. In a temperature of less than 40° C., the synthesis reaction of the organic acid metal salt hardly proceeds. A coating liquid for forming a magnesium oxide film obtained by dissolving an organic acid metal salt synthesized at a temperature exceeding 80° C. tends to have turbidity. Furthermore, this coating liquid is applied to a substrate and dried and baked, the formed magnesium oxide film may have turbidity.

In the solvent removing process after the salt formation reaction, it is preferable to remove the solvent at a temperature of 80° C. or less, more preferably 70° C. or less, and most preferably 60° C. or less. When the solvent is removed at a temperature exceeding 80° C., the dissolution speed of the resultant organic acid metal salt in an organic solvent is reduced significantly. Furthermore, the temporal stability of the coating liquid for forming a magnesium oxide film containing the obtained organic acid metal salt deteriorates. The solvent can be removed by a method commonly used by those skilled in the art. For example, a method of performing drying under reduced pressure, lyophilization, spray drying, or air blow drying can be employed. Typically, a method including a process of precipitating crystals from a reaction mixture, separating the precipitated crystals, and drying the crystals under reduced pressure is preferably employed. It is preferable that the solvent removal is performed in a time as short as possible.

The thus produced organic acid metal salt contains 99 wt % or more of the organic acid magnesium salt, and can be preferably used to form a magnesium oxide film.

The obtained organic acid metal salt can be dissolved in an alcohol solvent in a high concentration. This organic acid metal salt is dissolved in ethanol so that the ratio thereof is 40 wt % and the resultant solution is allowed to stand at 30° C. for one hour. In this case, the solution is clear (i.e., opaqueness is not obserbed).

The coating liquid for forming a magnesium oxide film of the present invention can be obtained by dissolving the organic acid metal salt of the present invention in an appropriate organic solvent. The coating liquid contains the organic acid metal salt of the present invention in a ratio of 1 to 100 parts by weight per 100 parts by weight of an organic solvent. When the content of the organic acid metal salt is less than 1 part by weight, the thickness of the formed magnesium oxide film is too small to be put to practical use. In order to increase the thickness, it is necessary to repeat coating and baking for a number of times, which deteriorates the productivity. When the content of the organic acid metal salt is more than 100 parts by weight, the organic acid magnesium salt is precipitated, so that uniform application cannot be performed and thus a uniform magnesium oxide film cannot be obtained.

The organic solvent used for the coating liquid can be selected from the group of an alcohol solvent and a mixed solvent containing an alcohol solvent. It is preferable to use a monohydric alcohol or a polyhydric alcohol having 1 to 8 carbon atoms as the alcohol solvent. If an alcohol solvent having 9 or more carbon atoms is used, it may be difficult to dissolve the organic acid metal salt of the present invention uniformly. Examples of the alcohol solvent include methanol, ethanol, propanol, butanol, pentanol, hexanol, heptanol, octanol, terpineol, ethylene glycol, and propylene glycol.

When a solvent having a comparatively high polarity such as methanol or ethanol is employed as the alcohol solvent in the coating liquid for forming a magnesium oxide film of the present invention, an organic acid metal salt derived from a saturated carboxylic acid having 4 to 6 carbon atoms, more preferably a saturated linear monocarboxylic acid having 4 to 6 carbon atoms can be employed as the organic acid metal salt. This may be applied to the case where the solvent used for the coating liquid is an alcohol solvent and the case where the solvent is a mixed solvent containing an alcohol solvent. When an alcohol having a high polarity is used as the alcohol solvent, the organic acid metal salt can be contained in the coating liquid in a higher concentration as the number of carbons of the saturated carboxylic acid is smaller.

On the other hand, when an alcohol having a comparatively low polarity such as butanol, pentanol, or hexanol is used as the alcohol solvent, an organic acid metal salt derived from a saturated carboxylic acid having 7 to 10 carbon atoms, more preferably a saturated linear monocarboxylic acid having 7 to 10 carbon atoms can be used as the organic acid metal salt. In this way, when an alcohol having a comparatively low polarity is used as the alcohol solvent, an organic acid metal salt can be contained in the coating liquid in a higher concentration by selecting the particular organic acid metal salt as described above.

As the solvent that is other than the alcohol solvent in a mixed solvent, it is preferable to use a solvent selected from the group consisting of an aliphatic hydrocarbon solvent, an ester solvent, an ether solvent, and a halogen solvent. The mixed solvent preferably contains an alcohol solvent in a ratio of 5 wt % or more, more preferably 30 wt % or more, and even more preferably 50 wt % or more. The mixed solvent containing 5 wt % or more of the alcohol solvent can dissolve the organic acid metal salt uniformly.

Examples of the aliphatic hydrocarbon solvent include n-hexane, octane, and cyclohexane.

Examples of the ester solvent include ethylene glycol monoethyl ether acetate, and propylene glycol monomethyl ether acetate.

Examples of the ether solvents include ethylene glycol monomethyl ether, ethylene glycol monoethyl ether, ethylene glycol monobutyl ether, propylene glycol monoethyl ether, and tetrahydrofuran.

Examples of the halogen solvent include dichloromethane and chloroform.

Any of the aliphatic hydrocarbon solvent, the halogen solvent, the ester solvent, and the ether solvent can be used alone or in combination with two or more to be mixed with the alcohol solvent.

Among the above solvents, ethanol, propanol, and n-butanol can be preferably used as the alcohol solvent. As solvents other than the alcohol solvent contained in the mixed solvent, ethylene glycol monoethyl ether, ethylene glycol monobutyl ether, propylene glycol monoethyl ether, propylene glycol monomethyl ether, ethylene glycol monoethyl ether acetate, or propylene glycol monomethyl ether acetate, or the like can be preferably employed.

The boiling point of the organic solvent used for the alcohol solvent or the mixed solvent is preferably 50° C. or more and 200° C. or less, most preferably 70° C. or more and 200° C. or less. When a coating liquid is prepared using a solvent having a boiling point of less than 50° C., the solvent tends to evaporate when being applied to a substrate, and irregularities in the coating tend to occur during application, and thus a uniform film is difficult to prepare. When a coating liquid is prepared using a solvent having a boiling point of more than 200° C., the solvent is not completely evaporated even at a temperature at which the organic acid metal salt starts to decompose when baking a coating film obtained from the coating liquid, and remains in the coating film. Therefore, the solvent that remains in the baking process decomposes, and the residue thereof remains inside the resultant magnesium oxide film. As a result, the electrical characteristics and the strength of the film may be affected adversely.

The coating liquid of the present invention may contain other metal organic acid salts, as long as it does not impair the effect of the present invention. Examples of the metal of other metal organic acid salts include calcium, strontium and barium classified in Group II; yttrium and elements of lanthanoide series (lanthanum, cerium, praseodymium, neodymium, samarium, europium, gadolinium, terbium, dysprosium, holmium, and the like) classified in Group III; titanium and zirconium classified in Group IV; vanadium and niobium classified in Group V; chromium classified in Group VI; manganese classified in Group VII; iron classified in Group VIII; cobalt classified in Group IX, nickel classified in Group X; copper, silver and gold classified in Group XI; zinc classified in Group XII; boron, aluminum, gallium and indium classified in Group XIII; silicon, germanium and tin classified in Group XIV; and antimony and bismuth classified in Group XV. Examples of the acid that forms the organic acid metal salt include acetic acid, octenoic acid, caproic acid, and naphthenic acid. Examples of the organic acid metal salts containing the above-mentioned elements include cobalt acetate, zinc acetate, silicon tetraacetate, tin octoate, tin caproate, tin naphthenate, and aluminum caproate.

The coating liquid of the present invention may contain additives such as a thickener, an antifoamer, a leveling agent, and the like, as long as they do not impair the effect of the present invention, that is, as long as they are dissolved uniformly in the solvent of the coating liquid. Examples of the thickener include cellulose compounds such as ethyl cellulose, cellulose nitrate, and the like; and organic acid magnesium salts having at least 13 carbon atoms such as magnesium tridecanoate, magnesium tetradecanoate, magnesium heptadecanoate, and magnesium octadecanoate. Examples of the antifoamer and the leveling agent include anionic surfactants, nonion surfactants, cationic surfactants, and polymer leveling agents.

There is no particular limitation regarding the method for coating a surface of a substrate with the organic acid metal salt of the present invention. For example, brush coating, dipping, spinning, spraying, screen printing, roll coating, or pattern formation by the inkjet method can be employed. A film obtained by these coating methods is dried and then baked, and thus a magnesium oxide film can be prepared. In order to convert the film obtained by the coating of the liquid containing the organic acid metal salt to a metal oxide film of the present invention, a method commonly used by those skilled in the art can be employed. For example, a method of baking the film at a temperature of 200° C. or more, a method of irradiating ultraviolet rays on the film or the like can be used. Furthermore, these methods can be employed in combination.

As a substrate on which the magnesium oxide film of the present invention is formed, a substrate used by those skilled in the art such as a glass substrate, a substrate made of a resin such as polycarbonate or epoxy resin, a resin film, and the like can be used. In particular, glass is preferable in order to form a metal oxide film by baking at a temperature of 200° C. or more. A resin substrate or a resin film is preferable in order to form a metal oxide film by irradiating ultraviolet light.

It is preferable to perform baking at 200° C. or more, more preferably 350° C. or more, and even more preferably 450° C. or more.

According to the present invention, an organic acid metal salt that is preferable to form a magnesium oxide film by the coating pyrolysis method. Such an organic acid metal salt has excellent temporal stability when it is formed into a coating liquid for forming a magnesium oxide film, and can provide a coating liquid for forming a coating film with high transparency. Using this coating liquid a film with high transparency is formed. This film is subjected to the process of baking, and then, a uniform magnesium oxide film with high transparency and no cracks can be obtained.

EXAMPLES

Hereinafter, a method for producing an organic acid metal salt of the present invention and a method for forming a magnesium oxide film by using this organic acid metal salt will be described specifically by way of examples. In the examples, "parts" indicates parts by weight.

[Raw Materials]

Table 1 shows raw materials (carboxylic acids) employed in the present invention and their purity along with other components (impurities) contained in the raw materials. The content of the impurities in each of the saturated monocarboxylic acid was quantified by gas chromatography.

TABLE 1

| Name of carboxylic acid | Purity of carboxylic acid | Content of other components (wt %) | | | |
|---|---|---|---|---|---|
| | | Paraffin compound | Ketone compound | Long chain alcohol compound | Long chain aldehyde compound |
| Butyric acid α | 99.5 | 0.4 | — | 0.1 | — |
| Butyric acid β | 96.0 | 2.9 | 0.9 | — | 0.2 |
| Valeric acid | 99.5 | 0.3 | 0.1 | — | 0.1 |
| Caproic acid α | 99.1 | 0.6 | 0.3 | — | — |
| Caproic acid β | 96.0 | 2.5 | 0.9 | 0.6 | — |
| Caprylic acid | 99.2 | 0.4 | 0.4 | — | — |
| Capric acid | 99.4 | 0.5 | — | 0.1 | — |
| Lauric acid | 99.9 | — | 0.1 | — | — |

In Table 1, the purity of butyric acid β and caproic acid β is less than 97% each, and does not meet the requirement of the component a to be employed in the present invention. The other saturated monocarboxylic acids meet the requirement of the component a.

[Method for Evaluating the Organic Acid Metal Salt]

(1) Content of Metal (Mg or Ca) in the Organic Acid Metal Salt

This content is quantified by fluorescent X-ray analysis.

(2) Content of an Organic Acid Magnesium Salt (Purity of Organic Acid Metal Salt)

About 10 g of a sample that had been dried at 110° C. for one hour was weighed (A (g)), and about 200 g of ion exchanged water was added thereto, followed by stirring for about one hour for dissolution while keeping the temperature of the liquid at 70° C. Then, the solution was filtrated with a membrane filter having a pore size of 0.5 μm that is made of polytetrafluoroethylene (PTFE). This filtrated liquid was evaporated under reduced pressure, and the residue was dried at 110° C. for one hour so that a white solid was obtained. Then, about 100 g of acetone was added to the obtained white solid, followed by stirring at 25° C. for 10 minutes and filtration with suction using a Buchner funnel. The white solid that remained on a filter paper was dried under reduced pressure at 80° C. for three hours and weighed precisely (B(g)). This white solid was ashed and then dissolved in a hydrochloric acid, and then the atomic absorption was measured so that the ratio of the magnesium in the total metal was measured (C). The content (wt %) of the organic acid magnesium salt was calculated based on the following equation.

Content (wt %) of the organic acid magnesium salt=$\{(B/A) \times C\} \times 100$ (3) Solubility of the Organic Acid Metal Salt in Ethanol The organic acid metal salt is dissolved in ethanol so that the concentration of the salt is 40 wt % and allowed to stand at 30° C. for one hour. Thereafter, the state of the solution was visually evaluated. The symbols in Tables 2 and 3 indicate the following evaluation results.

○ No opaqueness was observed.

x Turbidity or a precipitate was observed.

(4) Solubility of the Organic Acid Metal Salt in an Organic Solvent

The organic acid metal salt having a predetermined amount is dissolved in a solvent shown in Table 4 and allowed to stand at 30° C. for one hour. Thereafter, the state of the solution is visually evaluated. The symbols in Table 4 indicate the following evaluation results.

○ No opaqueness was observed.
Δ Some turbidity was observed.
x A precipitate was observed.

(5) Temporal Stability of the Coating Liquid Containing the Organic Acid Metal Salt The organic acid metal salt having a predetermined amount is dissolved in a solvent shown in Table 4 and allowed to stand at 30° C. for one hour. Thereafter, the solution is filtrated with a PTFE membrane filter having a pore size of 0.5 μm. The solution is allowed to stand at 30° C. for two weeks, and visually observed whether a white precipitate is caused in the solution. The symbols in Table 4 indicate the following evaluation results.

○ No opaqueness was observed.
Δ Some turbidity was observed.
x A precipitate was observed.

(6) Thickness of the Magnesium Oxide Film (MgO Film) Obtained by Baking

The thickness is measured with a stylus surface profilometer DEKTAC 3ST manufactured by ULVAC, Inc.

(7) Surface Appearance of the Magnesium Oxide Film Obtained by Baking

The surface of the film is observed with a stylus surface profilometer DEKTAC 3ST manufactured by ULVAC, Inc. Opaqueness and/or cracks of the film are observed. In the table, "presence" means that at least either one of them was observed, and "absence" means that neither of them was observed.

Example 1

Production of Organic Acid Metal Salt

First, 77.7 g (0.88 mol) of n-butyric acid, which is a saturated monocarboxylic acid (component a), 25.0 g (0.43 mol) of magnesium hydroxide, which is an inorganic magnesium compound (component b), and 300 g of water, which is a solvent, were added to a four-necked flask provided with a stirrer, a condenser, a thermometer, and a nitrogen inlet tube, and the resultant mixture was heated so that the internal temperature was increased to 60° C. while stirring the mixture under a nitrogen stream. Then, the mixture was stirred for another three hours, and thus a colorless and transparent aqueous solution was obtained. Thereafter, the mixture was cooled so that the internal temperature reached 50° C., and then the solvent was removed under reduced pressure, and thus an organic acid metal salt was obtained in an amount of 86.2 g in the form of a white solid.

About 10 g of this white solid was dried at 110° C. for one hour, and 9.9874 g (A) of the obtained sample was placed in a flask, and 190 g of ion exchanged water was added thereto, followed by stirring for one hour for dissolution while keeping the temperature of the mixture at 70° C. The resultant mixture was filtrated with a PTFE membrane filter having a pore size of 0.5 μm. Water in the filtrate was removed under reduced pressure with an evaporator and then dried in an oven at 110° C. for one hour, and thus a white solid was obtained. To this white solid, 100 g of acetone was added, and the mixture was stirred at 25° C. for 10 minutes, followed by filtration with suction using a Buchner funnel. The solid that remained on a filter paper was dried under reduced pressure at 80° C. for three hours, and the weight of the solid was measured and was found to be 9.9773 g (B). This white solid was heated at 800° C. for one hour for ashing and dissolved in 3 ml of 1N hydrochloric acid, and the atomic absorption was measured. The ratio of the magnesium with respect to the total metal was 0.996 (magnesium content: 99.6 wt %) (C). The content of the organic acid magnesium salt (the purity of the magnesium butyrate) calculated by the equation in the section (2) was 99.5 wt %.

Table 2 shows details of raw materials, solvent, reaction conditions employed in this example, and characteristics of the resultant organic acid magnesium salt. Table 2 also shows the results of Examples 2 to 7, which will be described later. In the same manner, Table 3 shows the results of Comparative Examples 1 to 10.

Example 2

Production of an Organic Acid Metal Salt

First, 89.3 g (0.87 mol) of n-valeric acid (saturated monocarboxylic acid; component a), and 25.0 g (0.43 mol) of magnesium hydroxide (inorganic magnesium compound; component b), and 300 g of water (solvent) were placed in a four-necked flask provided with a stirrer, a condenser, a thermometer and a nitrogen inlet tube, and the resultant mixture was heated so that the internal temperature was increased to 60° C. while stirring the mixture under a nitrogen stream. The mixture was stirred for another three hours, and thus a colorless and transparent aqueous solution was obtained. Thereafter, the solution was cooled to precipitate crystals and the precipitated crystals were filtrated and transferred to a stainless-steel vat and dried under reduced pressure at 50° C. Thus, an organic acid metal salt was obtained in an amount of 98.1 g in the form of a white solid.

About 10 g of this white solid was dried at 110° C. for one hour, and 10.0878 g (A) of the obtained sample was subjected to the same operation as in Example 1. Then, the dry weight (B) of the solid that remained on a filter paper was 10.0777 g, and the ratio of the magnesium contained (C) was 0.996. The content of the organic acid magnesium salt (the purity of the magnesium valerate) calculated by the equation in the section (2) was 99.5 wt %.

Example 3

Production of an Organic Acid Metal Salt

First, 101.6 g (0.87 mol) of n-caproic acid (saturated monocarboxylic acid; component a), 25.0 g (0.43 mol) of magnesium hydroxide (inorganic magnesium compound; component b), and 300 g of water (solvent) were added to a four-necked flask provided with a stirrer, a condenser, a thermometer, and a nitrogen inlet tube, and the resultant mixture was heated so that the internal temperature was increased to 55° C. while stirring the mixture under a nitrogen stream. Then, the mixture was stirred for another three hours, and thus a colorless and transparent aqueous solution was obtained. The solution was allowed to stand for cooling, followed by the removal of the solvent by lyophilization for 20 hours, and thus an organic acid metal salt was obtained in an amount of 101.3 g in the form of a white solid.

About 10 g of this white solid was dried at 110° C. for one hour, and 9.9564 g (A) of the obtained sample was subjected to the same operation as in Example 1. Then, the dry weight (B) of the solid that remained on a filter paper was 9.9464 g, and the ratio of the magnesium contained (C) was 0.996. The content of the organic acid magnesium salt (the purity of the magnesium caproate) calculated by the equation in the section (2) was 99.5 wt %.

Examples 4 and 5

An organic acid magnesium salt was produced in the same method as in Example 1 under the reaction conditions shown in Table 2, and evaluated.

Example 6

An organic acid magnesium salt was produced in the same method as in Example 3 under the reaction conditions shown in Table 2, and evaluated.

Example 7

An organic acid magnesium salt was produced in the same method as in Example 1 under the reaction conditions shown in Table 2, and evaluated.

Comparative Examples 1 to 10

An organic acid magnesium salt was produced in the same method as in Example 1 under the reaction conditions shown in Table 3, and evaluated

TABLE 2

| | Raw materials | | | | | Solvent | | Reaction conditions | | Characteristics of resultant organic acid metal salt | | |
| | Inorganic Mg compound | | Monocarboxylic acid | | | | Solvent (Water content; wt %) | Amount of solvent (g) | Reaction temperature (° C.) | Evaporation temperature (° C.) | Purity of organic acid metal salt*a (wt %) | Mg/Ca content in organic acid metal salt(wt %) | Solubility in ethanol |
| | Compound | Amount (g) | Compound | Amount (g) | Purity (%) | COOH/Mg | | | | | | | |
|---|---|---|---|---|---|---|---|---|---|---|---|---|---|
| Example 1 | Mg(OH)$_2$ | 25 0.43 mol | Butyric acid α | 77.7 | 99.5 | 2.06 | Water (100) | 300 | 60 | 50 | 99.5 | 99.6/0.2 | ○ |
| Example 2 | Mg(OH)$_2$ | 25 0.43 mol | Valeric acid | 89.3 | 99.5 | 2.04 | Water (100) | 300 | 60 | 50 | 99.5 | 99.6/0.2 | ○ |
| Example 3 | Mg(OH)$_2$ | 25 0.43 mol | Caproic acid α | 101.6 | 99.1 | 2.03 | Water (100) | 300 | 55 | −40 | 99.5 | 99.6/0.2 | ○ |
| Example 4 | Mg(OH)$_2$ | 25 0.43 mol | Caproic acid α | 101.6 | 99.1 | 2.03 | Water (100) | 300 | 60 | 60 | 99.6 | 99.8/0.1 | ○ |
| Example 5 | Mg(OH)$_2$ | 25 0.43 mol | Caproic acid α | 124.8 | 99.1 | 2.49 | Water (100) | 300 | 55 | 60 | 99.5 | 99.6/0.2 | ○ |
| Example 6 | Mg(OH)$_2$ | 25 0.43 mol | Caprylic acid | 127.1 | 99.2 | 2.05 | Water/ethanol (75) | 350 | 55 | −40 | 99.5 | 99.6/0.2 | ○ |
| Example 7 | Mg(OH)$_2$ | 25 0.43 mol | Capric acid | 151.8 | 99.4 | 2.05 | Water/ethanol (25) | 400 | 60 | 60 | 99.5 | 99.6/0.2 | ○ |

*a Content of organic acid magnesium salt in the resultant organic acid metal salt

TABLE 3

| | Raw materials | | | | | Solvent | | Reaction conditions | | Characteristics of resultant organic acid metal salt | | |
| | Inorganic Mg compound | | Monocarboxylic acid | | | | Solvent (Water content; wt %) | Amount of solvent (g) | Reaction temperature (° C.) | Evaporation temperature (° C.) | Purity of organic acid metal salt*a (wt %) | Mg/Ca content in organic acid metal salt(wt %) | Solubility in ethanol |
| | Compound | Amount (g) | Compound | Amount (g) | Purity (%) | COOH/Mg | | | | | | | |
|---|---|---|---|---|---|---|---|---|---|---|---|---|---|
| Comparative example 1 | Mg(OH)$_2$ | 25 0.43 mol | Lauric acid | 173.5 | 99.9 | 2.03 | Water/ethanol (33) | 600 | 60 | 60 | 99.4 | 99.6/0.2 | X |
| Comparative example 2 | Mg(OH)$_2$ | 25 0.43 mol | Caproic acid β | 105.0 | 96.0 | 2.03 | Water (100) | 300 | 55 | 50 | 93.4 | 99.6/0.2 | X |
| Comparative | Mg(OH)$_2$ | 25 0.42 mol | Caproic acid α | 99.5 | 99.1 | 2.03 | Water (100) | 300 | 55 | 50 | 97.0 | 97.4/2.1 | X |

TABLE 3-continued

| | Raw materials | | | | | Solvent | | Reaction conditions | | Characteristics of resultant organic acid metal salt | | |
|---|---|---|---|---|---|---|---|---|---|---|---|---|
| | Inorganic Mg compound | | Monocarboxylic acid | | | | Solvent (Water | Amount of | Reaction temperature | Evaporation temperature | Purity of organic acid metal salt*a | Mg/Ca content in organic acid metal salt | Solubility |
| | Compound | Amount (g) | Compound | Amount (g) | Purity (%) | COOH/ Mg | content; wt %) | solvent (g) | (° C.) | (° C.) | (wt %) | (wt %) | in ethanol |
| example 3 | | | | | | | | | | | | | |
| Comparative example 4 | Mg(OH)₂ | 25 0.43 mol | Butyric acid β | 79.6 | 96.0 | 2.03 | Water (100) | 300 | 60 | 60 | 92.3 | 99.6/0.2 | X |
| Comparative example 5 | Mg(OH)₂ | 25 0.42 mol | Caprylic acid | 124.0 | 99.2 | 2.03 | Water (100) | 300 | 60 | 60 | 97.3 | 97.8/1.9 | X |
| Comparative example 6 | Mg(OH)₂ | 25 0.43 mol | Caproic acid β | 98.0 | 96.0 | 1.90 | Water (100) | 300 | 60 | 60 | 89.3 | 99.6/0.2 | X |
| Comparative example 7 | Mg(OH)₂ | 25 0.43 mol | Caproic acid β | 206.5 | 96.0 | 4.00 | Water (100) | 300 | 60 | 60 | 90.2 | 99.6/0.2 | X |
| Comparative example 8 | Mg(OH)₂ | 25 0.43 mol | Lauric acid | 180.0 | 99.9 | 2.10 | Water/ ethanol (5) | 500 | 70 | 50 | 98.2 | 99.6/0.2 | X |
| Comparative example 9 | Mg(OH)₂ | 25 0.42 mol | Caproic acid α | 99.5 | 99.1 | 2.03 | Water (100) | 300 | 60 | 100 | 95.6 | 97.4/2.3 | X |
| Comparative example 10 | Mg(OH)₂ | 25 0.43 mol | Caproic acid β | 105.0 | 96.0 | 2.03 | Water (100) | 300 | 100 | 100 | 90.1 | 99.6/0.2 | X |

*a Content of organic acid magnesium salt in the resultant organic acid metal salt Preparation of Coating Liquids 1 to 23 and Preparation of Magnesium Oxide Films Each of the organic acid metal salts produced in Examples 1 to 7 and Comparative Examples 1 to 10 was dissolved in each of the organic solvents shown in Table 4 to prepare a coating liquid. The boiling point of the organic solvent employed was as follows: ethanol, 78° C.; 1-propanol, 97° C.; 1-butanol, 117° C.; 1-hexanol, 156° C.; 1-octanol, 196° C.; ethylene glycol, 197° C.; octane, 126° C.; PGMEA, 145° C.; EGMEA, 145° C.; PGME, 118° C.; EGME, 124° C.; PGEE, 132° C.; and EGBE, 170° C. This coating liquid was filtrated with a PTFE membrane filter having a pore size of 0.5 μm, and by using the resultant filtrate, a film of an organic acid magnesium salt was formed on a glass substrate with a spinning coater. In the case of coating liquid 2, filtration with a membrane filter was not performed. The resultant glass substrate was placed in a baking furnace and heated to 450° C. at a rate of 5° C./min in an air atmosphere, and thus a metal oxide film was obtained.

The coating liquids prepared by using the organic acid metal salts obtained in the examples of the present invention and the metal oxide (magnesium oxide) films derived from these coating liquids were evaluated based on the above-described methods. Table 4 shows the source of each of the organic acid metal salt, the solvent used, the concentration of the organic acid magnesium salt, the solubility of the organic acid metal salt in the organic solvent, the temporal stability of the coating liquid, the thickness of the magnesium oxide film obtained by baking, and the surface appearance thereof.

TABLE 4

| Coating liquid | Organic acid metal salt | Solvent (weight ratio) | Concentration of organic acid metal salt (wt %) | Solubility in organic slovent | Temporal stability of coating liquid | Thickness of MgO film (μm) | Surface appearance of MgO film (opaqueness and/or crack) |
|---|---|---|---|---|---|---|---|
| Coating liquid 1 | Example 1 | Ethanol/PGMEA = 1/0.5 | 30 | ○ | ○ | 0.6 | Absent |
| Coating liquid 2 | Example 2 | Ethanol/EGMEA = 1/1 | 30 | ○ | ○ | 0.4 | Absent |

TABLE 4-continued

| Coating liquid | Organic acid metal salt | Solvent (weight ratio) | Concentration of organic acid metal salt (wt %) | Solubility in organic slovent | Temporal stability of coating liquid | Thickness of MgO film (μm) | Surface appearance of MgO film (opaqueness and/or crack) |
|---|---|---|---|---|---|---|---|
| Coating liquid 3 | Example 3 | Ethanol/PGMEA = 1/0.8 | 40 | ○ | ○ | 0.5 | Absent |
| Coating liquid 4 | Example 3 | 1-Butanol/EGMEA = 1/0.8 | 30 | ○ | ○ | 0.4 | Absent |
| Coating liquid 5 | Example 3 | 1-Hexanol/PGME = 1/0.5 | 30 | ○ | ○ | 0.4 | Absent |
| Coating liquid 6 | Example 3 | 1-Octanol/PGEE = 1/0.5 | 30 | ○ | ○ | 0.4 | Absent |
| Coating liquid 7 | Example 3 | Ethylene glycol/PGMEA = 1/0.5 | 30 | ○ | ○ | 0.4 | Absent |
| Coating liquid 8 | Example 3 | Octane/ethanol/PGMEA = 0.2/0.8/0.8 | 30 | ○ | ○ | 0.4 | Absent |
| Coating liquid 9 | Example 4 | 1-Propanol/PGMAC = 1/1 | 30 | ○ | ○ | 0.4 | Absent |
| Coating liquid 10 | Example 5 | Ethanol/EGBE = 1/0.5 | 40 | ○ | ○ | 0.5 | Absent |
| Coating liquid 11 | Example 6 | 1-Octanol/EGME = 1/0.7 | 30 | ○ | ○ | 0.5 | Absent |
| Coating liquid 12 | Example 6 | 1-Butanol | 50 | ○ | ○ | 1.0 | Absent |
| Coating liquid 13 | Example 7 | Ethanol/EGBE = 1/0.5 | 30 | ○ | ○ | 0.4 | Absent |
| Coating liquid 14 | Comparative example 1 | Ethanol/PGMEA = 1/0.5 | 10 | X | — | — | — |
| Coating liquid 15 | Comparative example 2 | Ethanol/EGMEA = 1/1 | 20 | X | Δ | 0.2 | Absent |
| Coating liquid 16 | Comparative example 3 | Ethanol/PGME = 1/0.6 | 40 | Δ | X | 0.3 | Present |
| Coating liquid 17 | Comparative example 4 | 1-Butanol/EGME = 1/0.5 | 30 | X | Δ | 0.3 | Absent |
| Coating liquid 18 | Comparative example 5 | Ethanol/PGEE = 1/0.8 | 20 | Δ | X | 0.2 | Present |
| Coating liquid 19 | Comparative example 6 | Ethanol/PGMEA = 1/0.8 | 20 | X | Δ | 0.1 | Absent |
| Coating liquid 20 | Comparative example 7 | Ethanol/PGMEA = 1/0.8 | 20 | ○ | ○ | 0.08 | Absent |
| Coating liquid 21 | Comparative example 8 | Ethanol/PGMEA = 1/0.8 | 20 | X | — | — | — |
| Coating liquid 22 | Comparative example 9 | Ethanol/PGMEA = 1/0.8 | 20 | X | Δ | 0.1 | Absent |
| Coating liquid 23 | Comparative example 10 | Ethanol/PGMEA = 1/0.8 | 20 | X | Δ | 0.1 | Absent |

PGMEA: Propylene glycol monomethyl ether acetate
PGME: Propylene glycol monomethyl ether
PGEE: Propylene glycol monoethyl ether
EGMEA: Ethylene glycol monomethyl ether acetate
EGME: Ethylene glycol monoethyl ether
EGBE: Ethylene glycol monobutyl ether As seen from Table 2, all the organic acid metal salts of Examples 1 to 7 are those obtained from a saturated monocarboxylic acid having 97 wt % or more of a saturated monocarboxylic acid having 4 to 10 carbon atoms and an inorganic magnesium compound, and contain 99 wt % or more of an organic acid magnesium salt. Such an organic acid metal salt has excellent solubility in various solvents used for coating liquids, and provides high temporal stability to the obtained coating liquids. As shown in Table 4, a transparent magnesium oxide film without opaqueness and cracks was formed by baking a coating film derived from the coating liquid containing the organic acid metal salts of Examples 1 to 7. In the coating liquid 2, an excellent film was formed, although filtration with a membrane filter was not performed.

Furthermore, as seen from Table 2, all the organic acid metal salts of Examples 1 to 7 were synthesized by using magnesium hydroxide as the inorganic magnesium compound and reacting a saturated monocarboxylic acid having 4 to 10 carbon atoms in a slightly larger amount (between 2 and 2.5 moles) with respect to one mol of the magnesium hydroxide. In all the examples, a synthetic reaction was performed in an organic solvent containing 10 wt % or more of water, and the process of removing the solvent at a temperature of 80° C. or less was included.

On the other hand, as seen from Table 3, in the organic acid metal salts of Comparative Examples 1 and 8, the component a used is a saturated monocarboxylic acid having 12 carbon atoms. In the organic acid metal salts of Comparative Examples 2, 4 and 10, the purity of the saturated monocarboxylic acid used, which is the component a used, is less than 97 wt %. In Comparative Examples 3, 5 and 9, although a saturated monocarboxylic acid, which is the component a, having a purity of more than 97 wt %, was used, the content of the organic acid magnesium salt of the obtained organic acid metal salt was less than 99 wt %. Furthermore, as seen from Table 4, the organic acid metal salt in which the content of the organic acid magnesium salt is less than 99 wt % has low solubility in a solvent, and results in a coating liquid having poor temporal stability. Opaqueness and cracks were observed in each of the magnesium oxide films derived from the coating liquid containing the organic acid metal salts of Comparative Example 3 or 5. The organic acid metal salts of Comparative Examples 1 and 8 had very poor solubility in alcohol solvents and could not be formed into a coating liquid.

In Comparative Example 6, the saturated monocarboxylic acid in an amount of less than 2 moles with respect to one mole of the inorganic magnesium compound was reacted. In Comparative Example 7, the saturated monocarboxylic acid in an amount of more than 3.0 moles with respect to one mole of the inorganic magnesium compound was reacted.

As seen from Table 4, the organic acid metal salts obtained by the methods of Comparative Examples 6 and 10 have very poor solubility in solvents, and results in a coating liquid having poor temporal stability. A large amount of insoluble components remained in the coating liquid in which each of these organic acid metal salts was dissolved. Each of the coating liquids was filtrated with a membrane filter before coating a glass substrate, and then the substrate was coated with the coating liquid. The magnesium oxide film obtained after baking was too thin to be put to practical use. The organic acid metal salt obtained by the method of Comparative Example 7 had no problem with the solubility in solvents or the temporal stability of the resultant coating liquid. However, since the carboxylic acid was used in an excessive amount in the synthesis step, consequently the metal content was very low. Therefore, a magnesium oxide film obtained by baking a film prepared by using a coating liquid including the organic acid metal salt of Comparative Example 7 was too thin to be put to practical use. This would be because caproic acid (caproic acid β) having a purity of less than 97% was used. Furthermore, since the caproic acid was used in an excessive amount (four moles), the unreacted caproic acid would be brought into the coating liquid.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An organic acid metal salt obtained by reacting a saturated monocarboxylic acid or its salt and an inorganic magnesium compound,
   wherein the saturated moncarboxylic acid or its salt contains at least 97 wt % of a saturated monocarboxylic acid having 4 to 10 carbon atoms or its salt,
   wherein the saturated monocarboxylic acid or its salt contains impurities in an amount of 3 wt % or less, wherein the impurities are compounds selected from the group consisting of paraffin compounds, ketone compounds, long chain aldehydes, carboxylic acids having 3 carbon atoms or less, and carboxylic acids having at least 11 carbon atoms,
   wherein the molar ratio of the inorganic magnesium compound and the saturated monocarboxylic acid or its salt is 1:2.02 to 1:3 and the reaction is conducted in water or an organic solvent containing 10 wt % or more of water,
   wherein the organic acid metal salt contains at least 99 wt % of an organic acid magnesium salt, and
   wherein the organic acid metal salt is characterized in that a solution prepared by dissolving the organic acid metal salt in ethanol at a concentration of 40 wt % is clear after the solution is allowed to stand at 30° C. for one hour.

2. The organic acid metal salt of claim 1, wherein the saturated monocarboxylic acid having 4 to 10 carbon atoms is a saturated linear monocarboxylic acid.

3. A coating liquid for forming a magnesium oxide film, comprising,
   100 parts by weight of an organic solvent selected from the group consisting of an alcohol solvent and a mixed solvent that contains an alcohol solvent, and
   1 to 100 parts by weight of an organic acid metal salt according to claim 2.

4. The coating liquid of claim 3, wherein the alcohol solvent is monohydric or polyhydric alcohol having 1 to 8 carbon atoms.

5. A coating liquid for forming a magnesium oxide film, comprising,
   100 parts by weight of an organic solvent selected from the group consisting of an alcohol solvent and a mixed solvent that contains an alcohol solvent, and
   1 to 100 parts by weight of an organic acid metal salt according to claim 1.

6. The coating liquid of claim 5, wherein the mixed solvent is a mixed solvent of an alcohol solvent and a solvent selected from the group consisting of an aliphatic hydrocarbon solvent, an ester solvent, an ether solvent and a halogen solvent.

7. The coating liquid of claim 5, wherein the mixed solvent contains at least 5 wt % of an alcohol solvent.

8. The coating liquid of claim 5, wherein the alcohol solvent is monohydric or polyhydric alcohol having 1 to 8 carbon atoms.

9. The coating liquid of claim 5, wherein each of the boiling point of the alcohol solvent and the boiling point of the organic solvent contained in the mixed solvent is 70° C. or more and 200° C. or less.

10. The organic acid metal salt of claim 1, wherein the organic acid metal salt contains at least 99.5 wt % of an organic acid magnesium salt.

11. The organic acid metal salt of claim 1, wherein the inorganic magnesium compound is magnesium hydroxide.

12. A method for producing an organic acid metal salt, comprising the step of,
    reacting an inorganic magnesium compound with a saturated monocarboxylic acid or its salt in a molar ratio of 1:2.02 to 1:3 in water or an organic solvent containing 10 wt % or more of water,
    wherein the saturated monocarboxylic acid or its salt contains at least 97 wt % of a saturated monocarboxylic acid or its salt having 4 to 10 carbon atoms,
    wherein the saturated monocarboxylic acid or its salt contains impurities in an amount of 3 wt % or less, wherein the impurities are compounds selected from the group consisting of paraffin compounds, ketone compounds, long chain aldehydes, carboxylic acids having 3 carbon atoms or less, and carboxylic acids having at least 11 carbon atoms,
    wherein the organic acid metal salt contains at least 99 wt % of an organic acid magnesium salt, and
    wherein the organic acid metal salt is characterized in that a solution prepared by dissolving the organic acid metal salt in ethanol at a concentration of 40 wt % is clear after the solution is allowed to stand at 30° C. for one hour.

13. The method of claim 12, wherein the saturated monocarboxylic acid having 4 to 10 carbon atoms is a saturated linear monocarboxylic acid.

14. The method of claim 13, wherein the saturated monocarboxylic acid or its salt is a saturated monocarboxylic acid.

15. The method of claim 13, wherein the inorganic magnesium compound is magnesium hydroxide.

16. The method of claim 12, wherein the saturated monocarboxylic acid or its salt is a saturated monocarboxylic acid.

17. The method of claim 12, further comprising the step of removing the solvent at 80° C. or less.

18. The method of claim 12, wherein the inorganic magnesium compound is magnesium hydroxide.

19. A coating liquid for forming a magnesium oxide film, comprising, 100 parts by weight of an organic solvent selected from the group consisting of an alcohol solvent and a mixed solvent that contains an alcohol solvent, and 1 to 100 parts by weight of an organic acid metal salt produced according to the method of claim 4.

20. The coating liquid of claim 19, wherein the mixed solvent contains at least 5 wt % of an alcohol solvent.

* * * * *